US010049183B2

(12) United States Patent
Noh et al.

(10) Patent No.: US 10,049,183 B2
(45) Date of Patent: Aug. 14, 2018

(54) METHOD FOR ANALYZING HEALTH SIGNAL TO RESPOND TO INFECTIOUS DISEASE AND APPARATUS THEREOF

(71) Applicant: Samsung Electronics Co., Ltd., Suwon-si (KR)

(72) Inventors: Seungwoo Noh, Seongnam-si (KR); Younho Kim, Hwaseong-si (KR); Sangyun Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 17 days.

(21) Appl. No.: 15/206,528

(22) Filed: Jul. 11, 2016

(65) Prior Publication Data
US 2017/0270262 A1    Sep. 21, 2017

(30) Foreign Application Priority Data
Mar. 18, 2016 (KR) .................. 10-2016-0032714

(51) Int. Cl.
*A61B 5/00* (2006.01)
*A61B 5/0205* (2006.01)
(Continued)

(52) U.S. Cl.
CPC ...... *G06F 19/3418* (2013.01); *A61B 5/02055* (2013.01); *A61B 5/4266* (2013.01); *A61B 5/7282* (2013.01); *A61B 5/0002* (2013.01); *A61B 5/0015* (2013.01); *A61B 5/0022* (2013.01); *A61B 5/021* (2013.01);
(Continued)

(58) Field of Classification Search
CPC .......... G06F 19/30; G06F 19/32; G06F 19/34; G06F 19/3406; G06F 19/3418; G06F 19/3487; A61B 5/0002; A61B 5/0015; A61B 5/0004; A61B 5/0022; A61B 5/0024; A61B 5/02; A61B 5/742; A61B 5/743; A61B 5/735; A61B 5/746; A61B 5/7465; A61B 5/14532; A61B 5/02055; A61B 5/4266; A61B 5/7282; A61B 5/021; A61B 5/024; A61B 2560/0252; A61B 2562/029
See application file for complete search history.

(56) References Cited

U.S. PATENT DOCUMENTS 6,077,665 A * 6/2000 Weirich ............... G01N 33/569
435/6.1
6,238,337 B1    5/2001 Kambhatla et al.
(Continued)

FOREIGN PATENT DOCUMENTS

CN    104463753 A    3/2015
KR    10-2011-0137001 A    12/2011
(Continued)

*Primary Examiner* — Hai Phan
*Assistant Examiner* — Franklin Balseca
(74) *Attorney, Agent, or Firm* — NSIP Law (57) ABSTRACT

A method and an apparatus for analyzing a biosignal to respond to an infectious disease are provided. An analyzing method involves receiving biosignals of users of terminals and location information of the terminals, determining infectiousness of a condition of a user among the users by analyzing the location information and the biosignals, and transmitting feedback information regarding the infectiousness of the condition to one or more of the terminals.

20 Claims, 7 Drawing Sheets

(51) Int. Cl.
*A61B 5/021* (2006.01)
*A61B 5/024* (2006.01)
*G06F 19/00* (2018.01)

(52) U.S. Cl.
CPC ....... *A61B 5/024* (2013.01); *A61B 2560/0252* (2013.01); *A61B 2562/029* (2013.01)

(56) References Cited

U.S. PATENT DOCUMENTS

| | | |
|---|---|---|
| 7,993,266 B2 | 8/2011 | Colston, Jr. et al. |
| 2003/0129578 A1* | 7/2003 | Mault .................... G01N 33/50 435/4 |
| 2006/0036619 A1* | 2/2006 | Fuerst ................. G06F 19/3443 |
| 2008/0208009 A1* | 8/2008 | Shklarski ............. A61B 5/0022 600/301 |
| 2013/0054150 A1* | 2/2013 | Sacks ................ A61B 10/0012 702/19 |
| 2013/0268203 A1 | 10/2013 | Pyloth |
| 2014/0142448 A1* | 5/2014 | Bae .................... G06F 19/3418 600/515 |
| 2015/0100330 A1* | 4/2015 | Shpits ................ G06F 19/3493 705/2 |
| 2015/0227712 A1 | 8/2015 | Ryan et al. |
| 2016/0302733 A1* | 10/2016 | Lee ..................... A61B 5/7275 |

FOREIGN PATENT DOCUMENTS

| | | |
|---|---|---|
| KR | 10-2015-0076482 A | 7/2015 |
| KR | 10-2015-0077684 A | 7/2015 |
| KR | 10-2015-0102502 A | 9/2015 |

\* cited by examiner

| AM 9 | |
|---|---|
| AM 10 | |
| PM 1 | |
| PM 5 | |
| | |

420

| AM 9 | |
|---|---|
| AM 10 | Clean hospital |
| PM 2 | |
| PM 4 | |
| | |

430

| AM 9 | |
|---|---|
| PM 1 | |
| PM 3 | |
| | |
| | |

440

| AM 7 | |
|---|---|
| AM 8 | |
| AM 9 | |
| AM 10 | |
| AM 11 | Deliver to hospital |
| | |

450

| AM 7 | |
|---|---|
| AM 8 | |
| AM 9 | |
| AM 10 | See doctor |
| | |
| | |

METHOD FOR ANALYZING HEALTH SIGNAL TO RESPOND TO INFECTIOUS DISEASE AND APPARATUS THEREOF

CROSS-REFERENCE TO RELATED APPLICATIONS

This application claims the benefit under 35 USC 119(a) of Korean Patent Application No. 10-2016-0032714 filed on Mar. 18, 2016, in the Korean Intellectual Property Office, the entire disclosure of which is incorporated herein by reference for all purposes.

BACKGROUND

1. Field

The following description relates to a method and an apparatus for analyzing a biosignal to respond to the occurrence of an infectious disease.

2. Description of Related Art

Infectious diseases may cause a great burden to people due to the high transmission rate and the health impact, including the economic loss of work force and even a high rate of fatality. To prevent the transmission of an infectious disease, an early response by the community may be helpful. However, to launch an early response, the characteristics of the infectious disease should be rapidly understood, and then guidelines on how to diagnose the infectious disease should be prepared. A database for a plurality of patients may be used to store medical guidelines. However, such a database is expensive to set up and maintain, and much of the information in the database may be redundant or inconsistent. Thus, when a new type of infectious disease occurs, the database may limit how quickly a response to an infectious disease may be formulated. Recently, mobile devices that obtain biosignals of users have been introduced. A mobile device may obtain a biosignal of a user and provide it to a facility such as a hospital. Thus, mobile technology may be utilized to rapidly respond to the occurrence of a new infectious disease.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an analyzing method involves receiving biosignals of users of terminals and location information of the terminals, determining infectiousness of a condition of a user among the users by analyzing the location information and the biosignals, and transmitting feedback information regarding the infectiousness of the condition to one or more of the terminals.

The determining may be performed by a processor of an analyzing server, and the transmitting may be performed by a communicator of the analyzing server.

The determining may involve extracting singular signals from the biosignals by comparing the biosignals to one or more reference patterns, and determining whether a singular signal among the singular signals indicates an infectious disease by analyzing a similarity among the singular signals and a similarity among areas corresponding to the location information.

The general aspect of the method may further involve classifying users having symptoms of infection as a group suspected to have an infectious disease.

The general aspect of the method may further involve collecting environment information on an area corresponding to the location information, wherein the determining may involve determining whether the condition of the user indicates an infectious disease based on the location information, the biosignals, and the environment information.

The environment information may include at least one of a temperature of the area, a humidity of the area, or a type of a facility located in the area.

The general aspect of the method may further involve determining an infection expected area in which a spread of infection is estimated based on movement paths of the users having symptoms of an infectious disease.

The general aspect of the method may further involve receiving schedule information of the users and schedule information of a super spreader having a symptom of infection, wherein the determining involves determining whether the condition of the user indicates infectiousness by comparing the schedule information of the users to the schedule information of the super spreader.

The general aspect of the method may further involve requesting information for an analysis from users who visited a target area during a target period.

The feedback information may include at least one of information on a possibility of infection by a disease, a recommendation to avoid an outdoor activity, or a recommendation associated with an outpatient service.

In another general aspect, an analyzing method involves: transmitting, to an analyzing server, location information of a terminal and a biosignal measured from a user; and receiving feedback information on infectiousness of a condition of the user from the analyzing server in response to a determination that the condition of the user indicates infectiousness based on the location information and the biosignal.

Whether the condition of the user indicates infectiousness may be determined based on a similarity between an area corresponding to the location information and areas corresponding to location information of other terminals and a similarity between the biosignal measured from the user and biosignals of other users.

Whether the condition of the user indicates infectiousness may be determined based on the location information, the biosignal, and environment information of an area corresponding to the location information.

The environment information may include at least one of a temperature of the area, a humidity of the area, or a type of a facility located in the area.

The feedback information may include an infection expected area in which a spread of infection is estimated based on movement paths of users having symptoms of infection.

The general aspect of the method may further involve receiving a request to provide the biosignal from the analyzing server in response to a determination that the user visited a target area during a target period.

Users having symptoms of infection may be determined by comparing schedule information of the users to schedule information of a super spreader.

The feedback information may include at least one of information on a possibility of infection by a disease, a recommendation to avoid an outdoor activity, or a recommendation associated with an outpatient service.

The biosignal may include at least one of temperature information, blood pressure information, heartbeat information, or perspiration information.

The general aspect of the method may further involve outputting a message of inquiry as to whether the biosignal is provided to the analyzing server in response to the biosignal being different from a reference pattern, wherein the transmitting involves transmitting the location information and the biosignal to the analyzing server based on a user input in response to the message.

In yet another general aspect, a terminal includes a sensor configured to measure a biosignal from a user, and a communicator configured to transmit the biosignal and location information of the terminal to an analyzing server, and receive feedback information on infectiousness of a condition of the user from the analyzing server in response to a determination that the condition of the user indicates infectiousness based on the biosignal and the location information.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
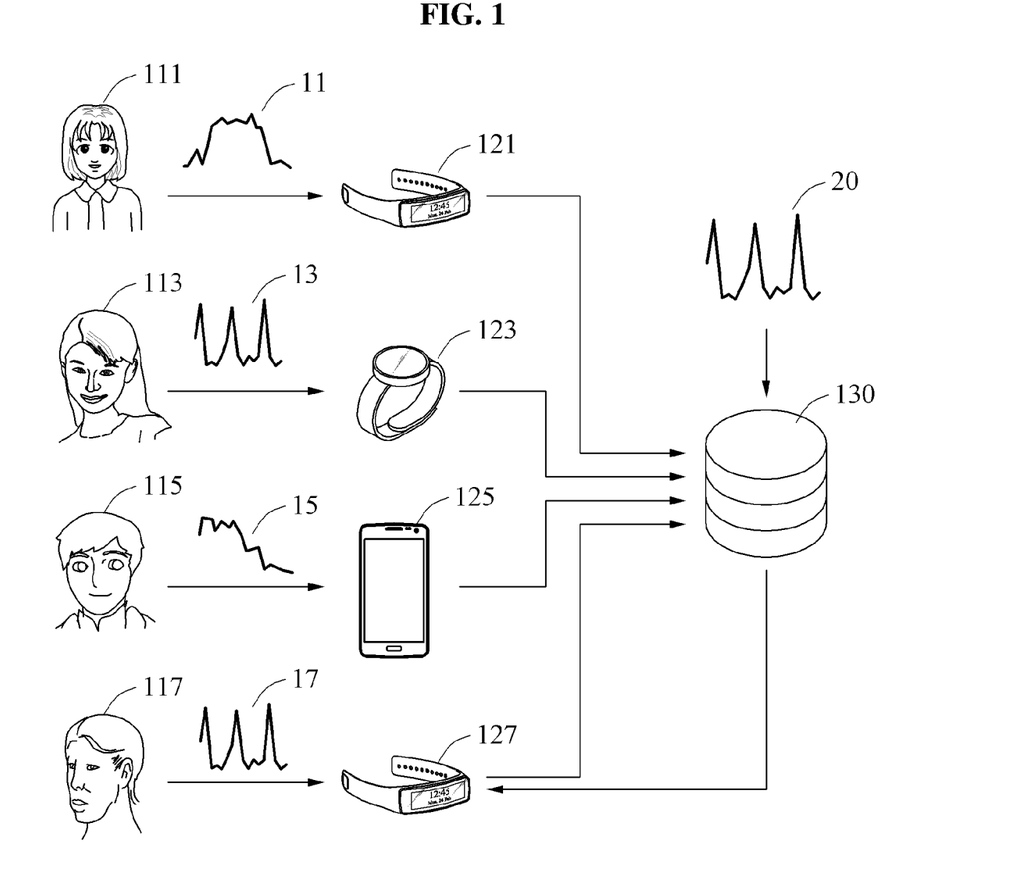
FIG. 1 illustrates examples of user terminals and an analyzing method performed by an analyzing server.

FIG. 1 illustrates examples of user terminals and an analyzing method of an analyzing server. Referring to FIG. 1, user terminals 121, 123, 125, and 127 measure a biosignal 11 of a first user 111, a biosignal 13 of a second user 113, a biosignal 15 of a third user 115, and a biosignal 17 of a fourth user 117, respectively. The user terminals 121, 123, 125, and 127 transmit the respective biosignals 11, 13, 15, and 17 to an analyzing server 130. The user terminals 121, 123, 125, and 127 transmit, to the analyzing server 130, location information of the user terminals 121, 123, 125, and 127 in addition to the biosignals 11, 13, 15, and 17.

The analyzing server 130 determines whether conditions of the users 111, 113, 115, and 117 indicate an occurrence of an infectious disease by analyzing the location information and the biosignals 11, 13, 15, and 17. The analyzing server 130 determines whether an unknown infectious disease may have occurred by analyzing the location information and the biosignals 11, 13, 15, and 17. For example, the analyzing server 130 detects an unusual phenomenon occurring among the users 111, 113, 115, and 117, and determines whether the phenomenon is associated with an infectious disease.

In an example, the analyzing server 130 extracts singular signals from the biosignals 11, 13, 15, and 17 by comparing each of the biosignals 11, 13, 15, and 17 to a reference pattern. The reference pattern refers to a pattern of a biosignal that is detected from each of the users 111, 113, 115, and 117 when their health condition is relatively normal. A singular signal refers to a signal having a difference greater than or equal to a predetermined threshold value compared to the reference pattern. A singular signal detected from a predetermined user indicates that a health condition of the user may be not normal.

The analyzing server 130 determines whether a user having the singular signal is suffering from an infectious disease. For example, the analyzing server 130 determines whether the singular signal indicates that a condition of the user is infectious by analyzing similarities between the singular signal from the user and the singular signals of other users and similarities with respect to the areas corresponding the location information of the user and the other users. In FIG. 1, the biosignal 13 and the biosignal 17 are assumed to be singular signals. The second user 113 and the fourth user 117 are infected by a predetermined infectious disease and thus, the biosignal 13 and the biosignal 17 measured from the user 113 and the user 117 exhibit a difference that is greater than or equal to a threshold compared to one or more reference patterns measured from the user 113 and the user 117 while they were healthy.

Referring to FIG. 1, the biosignal 13 and the biosignal 17 may have a similar pattern. Thus, the second user 113 and the fourth user 117 may be determined to be infected by a similar disease. Provided that the infectious disease being investigated is highly transmittable by a vector, the location information of the user terminals 121, 123, 125, and 127 and movement lines based on the location information may be considered in addition to the biosignals 11, 13, 15, and 17. By considering the biosignals 11, 13, 15, and 17 and the location information, the accuracy of determining whether conditions of the second user 113 and the fourth user 117 indicate an infectious disease may be enhanced.

The analyzing server 130 classifies the second user 113 and the fourth user 117 having symptoms of an infectious disease as a group suspected to be infected by the infectious disease. The analyzing server 130 changes the suspected group to a definite diagnosis group based on definite diagnosis information including a consultation guide for a definite diagnosis. The suspected group includes users suspected to be infected by the infectious disease, and the definite diagnosis group includes users having a relatively high possibility of being diagnosed as having the infectious disease. The analyzing server 130 receives a biosignal 20 of a definitely diagnosed patient. The biosignal 20 of the definitely diagnosed patient may be received from a disease control center. For example, the biosignal 20 may be from a patient whose condition has been confirmed by a health professional of the disease control center. The analyzing server 130 changes the suspected group to the definite diagnosis group based on the biosignal 20 of the definitely diagnosed patient. For example, the analyzing server 130 changes a group of a user having a biosignal from the suspected group to the definite diagnosis group based on a similarity between the biosignal 20 of the definitely diagnosed patient and the biosignal of the user of the suspected group.

The analyzing server 130 transmits feedback information on the infectiousness of the condition of a user to each of the user terminals 121, 123, 125, and 127. For example, the analyzing server 130 notifies the feedback information on the infectiousness of the health condition to users belonging to the suspected group and the definite diagnosis group. The feedback information includes at least one of information on a possibility of infection by a disease, a recommendation to avoid an outdoor activity, or a recommendation associated with an outpatient service, a vector suspected to be transmitting the infectious disease, and a route suspected to be infected by the infectious disease.

Figure 2:
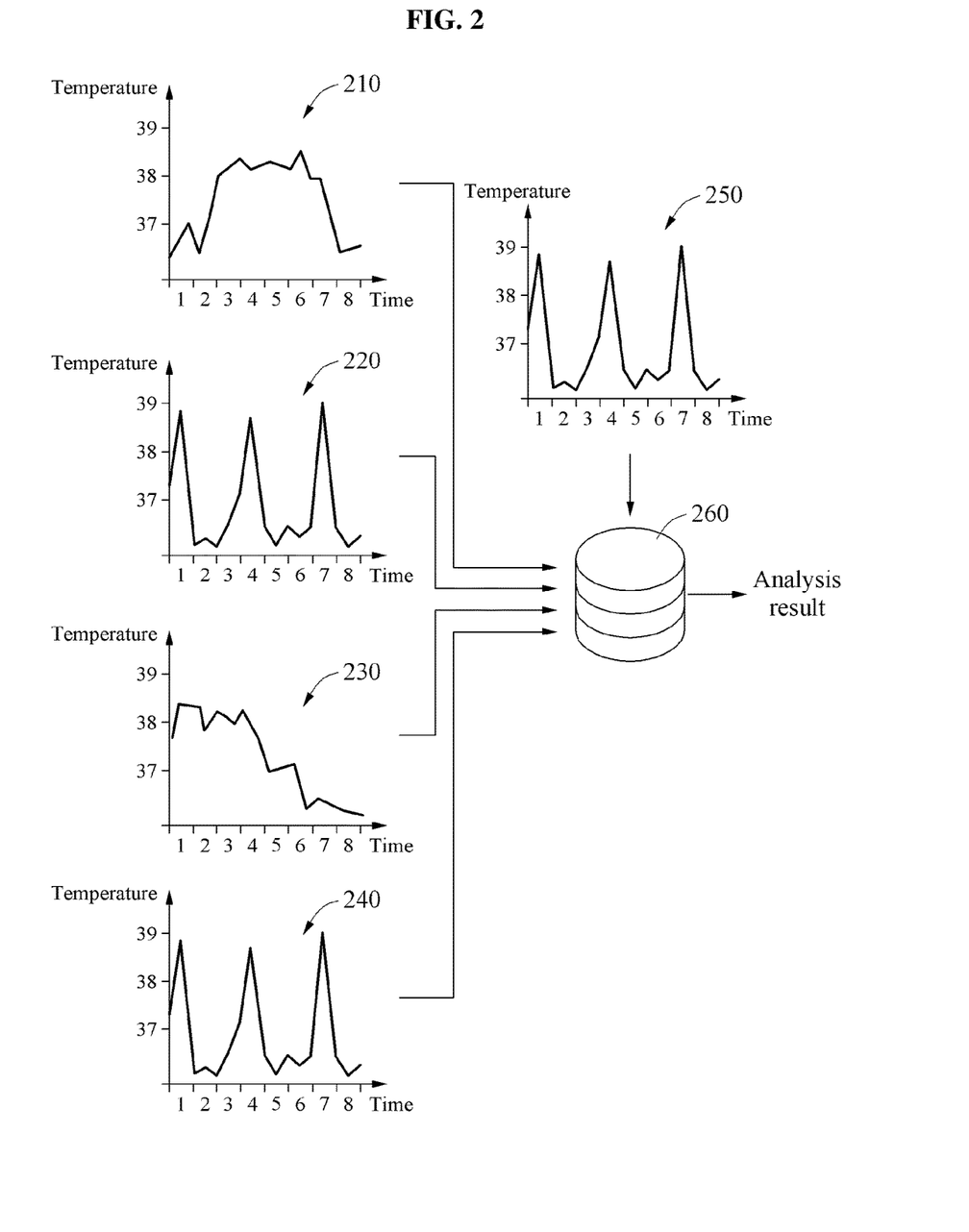
FIG. 2 illustrates an example of a method of analyzing a pattern.

FIG. 2 illustrates an example of a method of analyzing a pattern. Referring to FIG. 2, an analyzing server 260 receives each of biosignals 210, 220, 230, and 240 measured from users. The analyzing server 260 determines whether symptoms of the user indicate infectiousness based on the biosignals 210, 220, 230, and 240, and provides feedback information regarding the infectiousness of a condition of the user to user terminals. Each of the biosignals 210, 220, 230, and 240 include at least one of temperature information, blood pressure information, heartbeat information, or perspiration information. The user terminals measure respective biosignals 210, 220, 230, and 240 from the users using various types of sensors.

A user terminal provides a biosignal to the analyzing server 260 in response to a difference between the biosignal of the user and a reference pattern being different from a threshold range. The threshold range is determined based on the reference pattern corresponding to a biosignal measured from a user in a healthy condition. For example, the threshold range is determined based on a minimum temperature and a maximum temperature of the healthy condition. The user terminal determines that the user has an issue in response to a temperature of the user being lower than the minimum temperature or higher than the maximum temperature based on the reference range, and provides the biosignal to the analyzing server 260.

In an example, the threshold range is determined from a change in pattern. For example, the threshold range is determined based on a difference between the minimum temperature and the maximum temperature of the healthy condition or a time interval during which the temperature is the minimum temperature and the maximum temperature. The user terminal determines that the user has an issue in response to a change amount of a user temperature being greater than that of the threshold range or a time interval during which a change speed of the user's temperature is faster than that of the threshold range.

Each of the biosignals 210, 220, 230, and 240 has a pattern based on time. The pattern of each of the biosignals 210, 220, 230, and 240 may have a unique change amount based on time. Thus, the biosignals 210, 220, 230, and 240 may be used to specify health conditions of the users. For example, a user infected by a predetermined infectious disease may have a predetermined form of a temperature pattern or a predetermined form of a blood pressure pattern. Thus, whether the infectious disease is present may be determined based on a comparison of the biosignals 210, 220, 230, and 240.

Referring to FIG. 2, the biosignals 220, 230, and 240 are assumed to be different from the reference range. That is, it is assumed that conditions of the users may not be normal. Users of which biosignals are similar among the users having abnormal conditions may have been infected by a similar disease. For example, a pattern of the biosignal 220 measured from a second user is similar to a pattern of the biosignal 240 measured from a fourth user. Thus, the second user and the fourth user may be infected by a similar disease. When a number of users infected by the similar disease increases or exceeds a predetermined reference number, the disease may be determined to be an infectious disease. At an early stage at which the infectious disease starts to spread, symptoms of the second user and the fourth user may be determined to indicate infectiousness, and the second user and the fourth user may be managed and classified as a group suspected to be infected by the same infectious disease.

After the infectious disease spreads, there may be a patient that receives a definite diagnosis of being infected by the infectious disease. For example, the patient may be determined to have an infectious disease by a health professional. A consultation guide is determined from the definitely diagnosed patient, and a biosignal 250 is extracted from the definitely diagnosed patient. A definite diagnosis group is extracted from the users by comparing the biosignal 250 to each of the biosignals 210, 220, 230, and 240 measured from the users. For example, each of the biosignals 220 and 240 of the users classified as the suspected group is compared to the biosignal 250 of the definitely diagnosed patient, and the suspected group is changed to the definite diagnosis group based on a similarity between the biosignals 220 and 240, and the biosignal 250.

The infectious disease may be transmitted through a specific vector. Thus, whether the infectious disease is present is determined based on movement paths of the user. The movement paths of the user may be determined based on location information of a user terminal. The user terminal records the location information of the user terminal as time elapses, and provides the location information to the analyzing server 260. The analyzing server 260 generates an analysis result based on the location information and the biosignals 210, 220, 230, and 240. Based on the analysis result, feedback information on the infectiousness is determined.

The analyzing server 260 may consider a similarity of the movement paths based on the location information when the analysis result is generated. In an example, the analyzing server 260 includes, in the suspected group, users of which movement paths overlap among the users of which patterns based on the biosignals 210, 220, 230, and 240 are similar. For example, the analyzing server 260 includes, in the suspected group, users who visited a similar place during a similar period among the users of which the patterns based on the biosignals 210, 220, 230, and 240 are similar.

A transmission rate of the infectious disease may depend on a surrounding environment factor such as a temperature and a humidity of the area where the infectious disease is spreading. The infectious disease may spread at a specific facility such as a swimming pool or a hospital. Thus, environment information on surroundings of a movement line of the user may be used to determine whether the symptom of the user indicates infectiousness of the user's condition. The environment information includes at least one of a temperature of an area, a humidity of the area, or a type of a facility located in the area, as determined based on the location information. The analyzing server 260 collects the environment information on surroundings of movement lines of the users. The analyzing server 260 extracts the suspected group from the users based on the environment information and the location information, and the biosignals 210, 220, 230, and 240. For example, the analyzing server 260 includes, in the suspected group, users of which surrounding environments of movement lines are similar among users of which patterns based on the biosignals 210, 220, 230, and 240 are similar.

Figure 3:
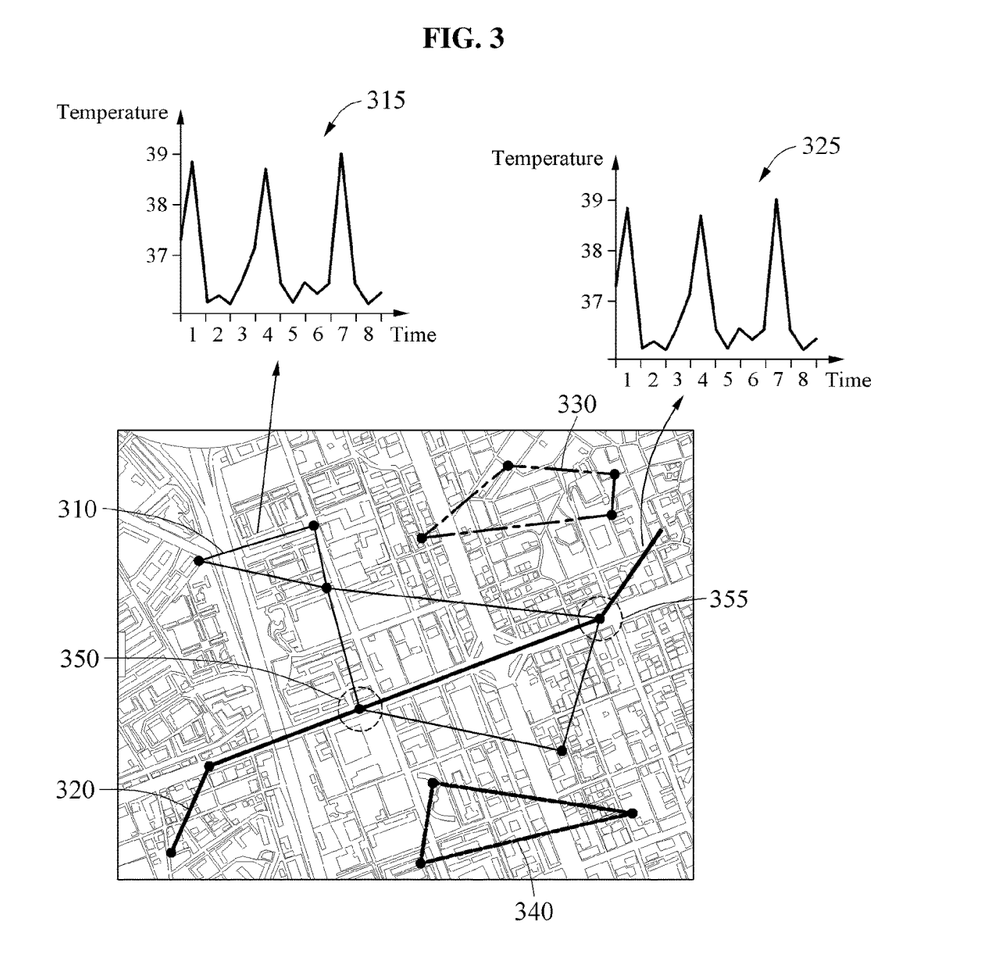
FIG. 3 illustrates an example of a method of analyzing a movement path.

FIG. 3 illustrates an example of a method of analyzing a movement path. FIG. 3 illustrates a movement path 310 of a first user, a movement path 320 of a second user, a movement path 330 of a third user, and a movement path 340 of a fourth user in a predetermined region. The movement paths of users and time information may be recorded, and the time information may be provided to an analyzing server. A biosignal 315 of the first user is assumed to be similar to a biosignal 325 of the second user.

The analyzing server learns the movement paths of the users based on location information provided from the terminals of the users. The analyzing server classifies the first user and the second user as a suspected group based on a similarity between the biosignal 315 and the biosignal 325, and a similarity between the movement path 310 and the movement path 320. In an example, the analyzing server determines an infection expected area in which a spread of infection is estimated based on the movement paths of the users having symptoms of an infectious disease. For example, the analyzing server determines, as the infection expected area, at least one of areas 350 and 355 in which movement paths of the suspected group overlap during a predetermined time.

The analyzing server collects environment information on the areas 350 and 355, and determines at least one of the areas 350 and 355 as the infection expected area based on the environment information. For example, the analyzing server determines an area having a temperature or a humidity associated with an infectious disease or an area in which a facility such as a swimming pool and a hospital is located, as the infection expected area from the areas 350 and 355.

Figure 4:
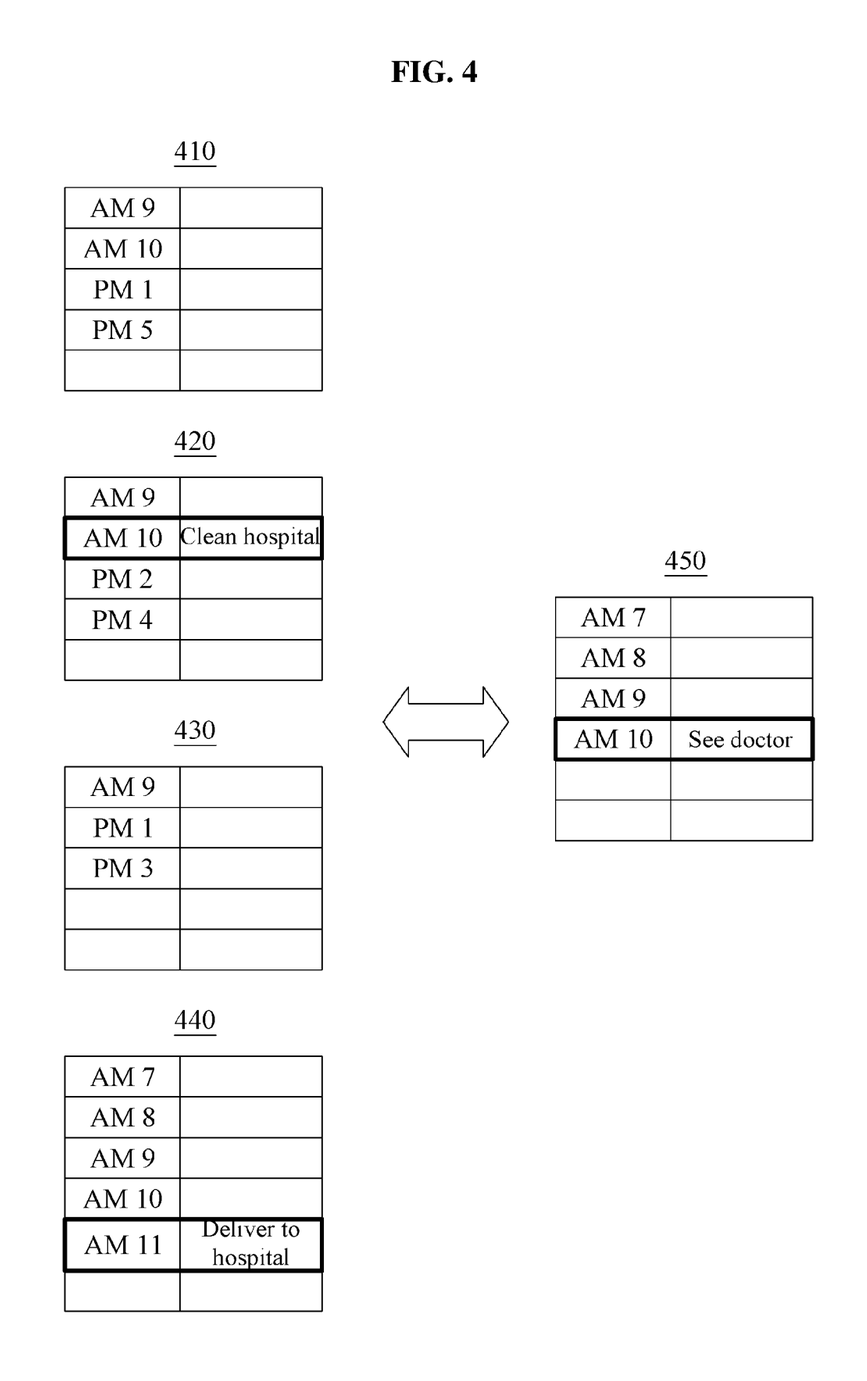
FIG. 4 illustrates an example of a method of analyzing schedule information.

FIG. 4 illustrates an example of a method of analyzing schedule information. FIG. 4 illustrates schedule information 410 of a first user, schedule information 420 of a second user, schedule information 430 of a third user, schedule information 440 of a fourth user, and schedule information 450 of a super spreader having a symptom of infection. Hereinafter, the users are referred to as the first user, the second user, the third user, and the fourth user. An analyzing server determines whether symptoms of the users and the super spreader indicate an infectious disease based on the schedule information 410, the schedule information 420, the schedule information 430, the schedule information 440, and the schedule information 450. The schedule information 410, the schedule information 420, the schedule information 430, and the schedule information 440 are received from respective user terminals of the first user, the second user, the third user, and the fourth user. The schedule information 450 may be received from a disease control center.

Since schedules of the users follow the schedule information 410, the schedule information 420, the schedule information 430, and the schedule information 440, activities of the users are specified based on the schedule information 410, the schedule information 420, the schedule information 430, and the schedule information 440. Since a transmission of an infectious disease is closely associated with the activities of the users, the schedule information 410, the schedule information 420, the schedule information 430, and the schedule information 440 are used to determine whether the users are infected by an infectious disease.

The analyzing server extracts a suspected group from the users by comparing each of the schedule information 410, the schedule information 420, the schedule information 430, and the schedule information 440 to the schedule information 450. For example, the analyzing server determines an activity of the super spreader based on the schedule information 450, and determines the activities of the users based on the schedule information 410, the schedule information 420, the schedule information 430, and the schedule information 440. The analyzing server determines whether the conditions of the users indicate the occurrence of an infectious disease by comparing each of the schedule information 410, the schedule information 420, the schedule information 430, and the schedule information 440 of the users to the schedule information 450 of the super spreader. Alternatively, the analyzing server extracts the suspected group from the users based on a similarity between the activity of the super spreader and each of the activities of the users.

In an example, a similarity of the schedules is determined based on a similarity of times at which activities based on schedule information are performed and a similarity of places where the activities are performed. For example, referring to FIG. 4, a similarity between the schedule information 420 and the schedule information 450 is determined to be relatively great since at 10 A.M. the super spreader is to see a doctor at a hospital and at 10 A.M. the second user is to clean the hospital. Referring to FIG. 4, a similarity between the schedule information 440 and the schedule information 450 is less than the similarity between the schedule information 420 and the schedule information 450 since at 11 A.M. the fourth user is to make a delivery to the hospital.

Figure 5:
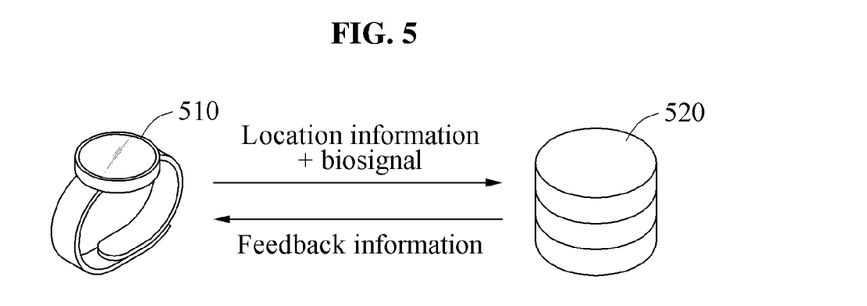
FIG. 5 illustrates an example of a method of transmitting location information and a biosignal.

FIG. 5 illustrates an example of a method of transmitting location information and a biosignal between a terminal 510 and an analyzing server 520. Referring to FIG. 5, the terminal 510 transmits location information and a biosignal to the analyzing server 520. The analyzing server 520 generates feedback information based on the location information and the biosignal, and transmits the feedback information to the terminal 510. The feedback information may be output to the user via various output devices, such as a display, a speaker or the like.

The terminal 510 continuously measures the biosignal of the user. For example, the terminal 510 may include a sensor to be disposed on a body part of the user. The terminal 510 builds a database for the biosignal of the user. A large volume database is used to store the biosignal of the user. In an example, the terminal 510 stores the data for the biosignal in an external device with more non-transitory memory storage space linked to the terminal. In another example, the terminal 510 stores the biosignal according to a predetermined sampling rate, or stores and filters a biosignal determined to be abnormal among continuously measured biosignals in an internal non-transitory memory storage. The terminal 510 provides the biosignal that is different from a threshold range to the analyzing server 520. As described above, the threshold range is determined based on the biosignal measured from a user in a healthy condition.

Since the location information and the biosignal are private information of the user, a method of providing the location information and the biosignal to the analyzing server 520 while protecting the privacy of the user may be requested. In an example, the user predetermines a condition for providing the location information and the biosignal. For example, the user sets the terminal 510 to provide the predetermined information of the biosignal to the analyzing server 520. In an example, the user sets the terminal 510 to provide the location information and temperature information that are different from the threshold range to the analyzing server 520 in response to the temperature information being different from the threshold range.

In another example, the terminal 510 provides the location information and the biosignal to the analyzing server 520 in response to a temporal request of the user. For example, the terminal 510 warns the user in response to the biosignal being different from the threshold range. The user temporarily requests the terminal 510 to provide the location information and the biosignal to the analyzing server 510 to check a health condition of the user. In this example, the terminal 510 provides the location information and the biosignal of the user to the analyzing server 520 in response to the temporal request of the user.

In still another example, the location information and the biosignal are provided to the analyzing server 520 in response to a request of the analyzing server 520 and an agreement of the user. In a process in which a medical team investigates the infectious disease, location information or biosignals of a predetermined group may be requested. In this example, the medical group may request the location information or the biosignals from the group through the analyzing server 520, and the location information or the biosignals of users may be provided to the analyzing server 520 in response to the users agreeing to provide the location information or the biosignals. For example, the analyzing server 520 requests information for an analysis from users who visited a target area during a target period.

Figure 6:
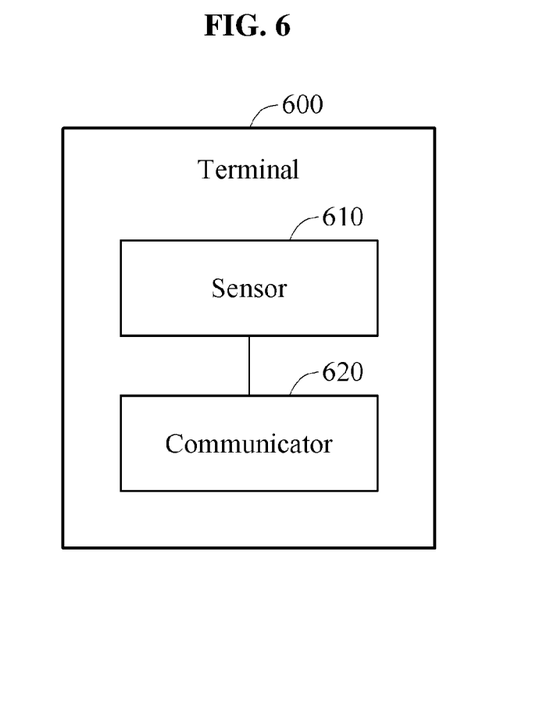
FIG. 6 is a block diagram illustrating an example of a terminal.

FIG. 6 is a block diagram illustrating an example of a terminal. Referring to FIG. 6, a terminal 600 includes a sensor 610 and a communicator 620. The sensor 610 and the communicator 620 are hardware components. The terminal 600 is provided in various electronic devices to determine whether a symptom of a user indicates an infectious disease. For example, the terminal 600 may be an electronic device such as a satellite wireless phone or a cellular phone, for example, a smartphone, a tablet computer, a laptop, and a personal digital assistant (PDA). The sensor 610 measures a biosignal from a user. The sensor 610 measures various biosignals. For example, the sensor 610 measures at least one of temperature information, blood pressure information, heartbeat information, or perspiration information. The terminal 600 transmits location information of the terminal 600 and the biosignal to the analyzing server, and receives feedback information on the infectiousness of a condition of a user from the analyzing server in response to a determination that the condition of the user is suspected to be infectious based on the location information and the biosignal. Although not illustrated in FIG. 6, the terminal 600 may include an outputter configured to output the feedback information, an inputter configured to receive an input of the user, and a storage configured to store the biosignal. The output device and the input device are hardware components. The outputter may include an output device such as a display screen or a speaker. The inputter may include an input device such as a touch screen, a button, a microphone, a camera, a sensor, and the like. Repeated descriptions will be omitted for increased clarity and conciseness because the aforementioned descriptions are also applicable to the terminal 600.

Figure 7:
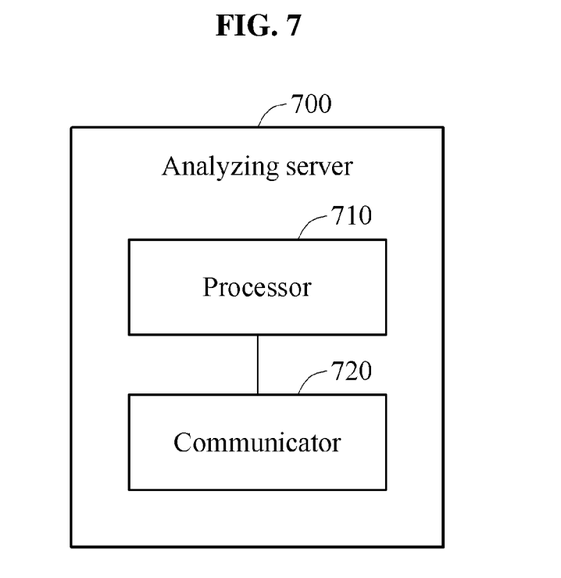
FIG. 7 is a block diagram illustrating an example of an analyzing server.

FIG. 7 is a block diagram illustrating an example of an analyzing server. Referring to FIG. 7, an analyzing server 700 includes a processor 710 and a communicator 720. The processor 710 and the communicator 720 are hardware components. The analyzing server 700 is provided in various electronic devices to determine whether a symptom of a user indicates infectiousness. For example, the analyzing server 700 may be an electronic device such as a satellite wireless phone or a cellular phone, for example, a smartphone, a tablet computer, a laptop, and a personal digital assistant (PDA). For example, the communicator 720 receives, from a plurality of terminals, location information of the terminals and biosignals measured from users of the terminals. The processor 710 determines whether symptoms of the users indicate an infectious disease by analyzing the location information and the biosignals. The communicator 720 transmits feedback information on the infectiousness of a user's condition to the terminals. Although not illustrated in FIG. 7, the analyzing server 700 may include an outputter configured to output the biosignals, an inputter configured to receive inputs of the users, and a non-transitory memory storage configured to store the biosignals. The output device and the input device are hardware components. Repeated descriptions will be omitted for increased clarity and conciseness because the aforementioned descriptions are also applicable to the terminal 700.

Figure 8:
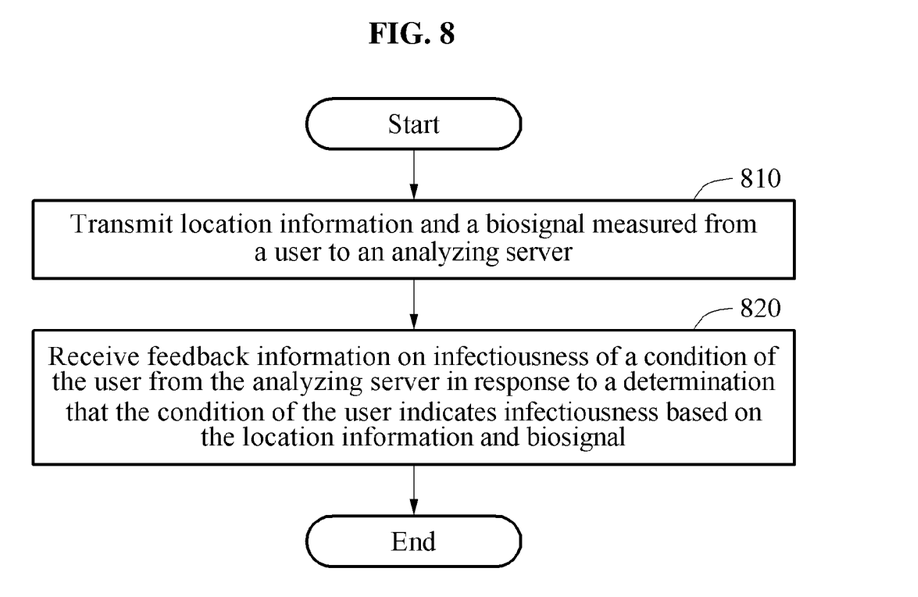
FIG. 8 is a flowchart illustrating an example of an analyzing method of a terminal.

FIG. 8 is a flowchart illustrating an example of an analyzing method performed by a terminal. Referring to FIG. 8, in operation 810, a terminal transmits location information and a biosignal measured from a user to an analyzing server. In operation 820, the terminal receives feedback information on the infectiousness of the user's condition from the analyzing server in response to a determination that a symptom of the user indicates an infectious disease based on the location information and the biosignal. Repeated descriptions will be omitted for increased clarity and conciseness because the aforementioned descriptions are also applicable to the analyzing method of the terminal.

Figure 9:
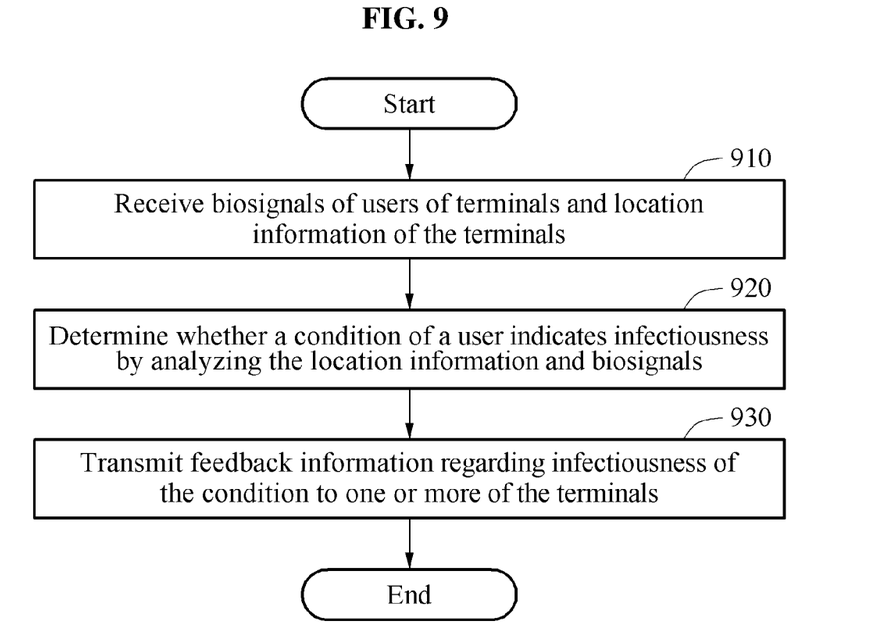
FIG. 9 is a flowchart illustrating an example of an analyzing method of an analyzing server.

FIG. 9 is a flowchart illustrating an example of an analyzing method performed by an analyzing server. Referring to FIG. 9, in operation 910, an analyzing server receives location information of a plurality of terminals and biosignals measured from users of the terminals. In operation 920, the analyzing server determines whether symptoms of the users indicate an infectious disease by analyzing the location information and the biosignals. In operation 930, the analyzing server transmits feedback information on the infectiousness of the user's condition to the terminals. Repeated descriptions will be omitted for increased clarity and conciseness because the aforementioned descriptions are also applicable to the analyzing method of the analyzing server.

The apparatuses, devices, sensors, communicators, processors, analyzing servers, terminals, mobile device, electronic device, inputter, outputter, and other components illustrated in FIGS. 6 and 7 that perform the operations described herein with respect to FIGS. 1-5, 8 and 9 are implemented by hardware components. Examples of hardware components include controllers, sensors, generators, drivers, memories, comparators, arithmetic logic units, adders, subtractors, multipliers, dividers, integrators, electrodes, antenna, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-5, 8 and 9. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-5, 8 and 9 may be performed by computing hardware, for example, by one or more processors or computers, as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

As a non-exhaustive example only, a terminal as described herein may be a mobile device, such as a cellular phone, a smart phone, a wearable smart device (such as a ring, a watch, a pair of glasses, a bracelet, an ankle bracelet, a belt, a necklace, an earring, a headband, a helmet, or a device embedded in clothing), a portable personal computer (PC) (such as a laptop, a notebook, a subnotebook, a netbook, or an ultra-mobile PC (UMPC), a tablet PC (tablet), a phablet, a personal digital assistant (PDA), a digital camera, a portable game console, an MP3 player, a portable/personal multimedia player (PMP), a handheld e-book, a global positioning system (GPS) navigation device, or a sensor, or a stationary device, such as a desktop PC, a high-definition television (HDTV), a DVD player, a Blu-ray player, a set-top box, or a home appliance, or any other mobile or stationary device capable of wireless or network communication. In one example, a wearable device is a device that is designed to be mountable directly on the body of the user, such as a pair of glasses or a bracelet. In another example, a wearable device is any device that is mounted on the body of the user using an attaching device, such as a smart phone or a tablet attached to the arm of a user using an armband, or hung around the neck of the user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An analyzing method comprising:
receiving biosignals of users of terminals using sensors integrated with the terminals and simultaneously acquired corresponding location information of the terminals;
extracting singular signals from the biosignals by comparing the biosignals to one or more reference patterns, the one or more reference patterns detected during a health condition of the users being relatively normal;
determining infectiousness of a condition of a first user among the users by analyzing a similarity among the singular signals and a similarity among areas corresponding to the corresponding location information;
classifying the first user as a suspected group, in response to the determining that the condition of the first user indicates infectiousness, wherein the suspected group comprises users suspected of having a disease condition;
receiving a biosignal of a second user from a definite diagnosis group having a confirmed disease condition;
changing the users in the suspected group to the definite diagnosis group, based on a comparison of a pattern of a biosignal of the first user and a pattern of the biosignal of the second user; and
transmitting feedback information on the infectiousness of the condition to a terminal of the first user.

2. The method of claim 1, wherein the determining is performed by a processor of an analyzing server, and the transmitting is performed by a communicator of the analyzing server.

3. The method of claim 1, further comprising:
classifying users as the suspected group in response to a determination that condition of the users indicates infection.

4. The method of claim 1, further comprising:
collecting environment information on an area corresponding to the location information,
wherein the determining comprises determining whether the condition of the user indicates an infectious disease based on the location information, the biosignals, and the environment information.

5. The method of claim 4, wherein the environment information comprises at least one of a temperature of the area, a humidity of the area, or a type of a facility located in the area.

6. The method of claim 3, further comprising:
determining an infection expected area in which a spread of the infection is estimated based on movement paths of the users having the condition indicating infection.

7. The method of claim 1, further comprising:
receiving schedule information of the users and schedule information of a super spreader having a condition indicating infection; and
determining whether conditions of the users indicate infectiousness by comparing the schedule information of the users to the schedule information of the super spreader.

8. The method of claim 1, further comprising:
requesting information for an analysis from users who visited a target area during a target period.

9. The method of claim 1, wherein the feedback information comprises at least one of information on a possibility of infection by a disease, a recommendation to avoid an outdoor activity, or a recommendation associated with an outpatient service.

10. An analyzing method comprising:
transmitting, to an analyzing server, location information of a terminal and a simultaneously acquired corresponding biosignal measured via sensors integrated in the terminal from a first user; and
receiving feedback information on infectiousness of a condition of the user from the analyzing server in response to a determination that the condition of the user indicates infectiousness based on the location information and the biosignal;
singular signals are extracted, by the analyzing server, from the biosignals of users of terminals by comparing the biosignals to one or more reference patterns, the one or more reference patterns detected during a health condition of the users being relatively normal;
the infectiousness of the condition of the first user among the users is determined, by the analyzing server, by analyzing a similarity among the singular signals and a similarity among areas corresponding to the corresponding location information;
the first user is classified as a suspected group, by the analyzing server, in response to the determining that the condition of the first user indicates infectiousness, wherein the suspected group comprises users suspected of having a disease condition;
a biosignal of a second user is received, by the analyzing server, the second user being from a definite diagnosis group having a confirmed disease condition;
the users in the suspected group are changed, by the analyzing server, to the definite diagnosis group, based on a comparison of a pattern of a biosignal of the first user and a pattern of the biosignal of the second user.

11. The method of claim 10, wherein whether the condition of the first user indicates infectiousness is determined based on a similarity between an area corresponding to the location information and areas corresponding to location information of other terminals and a similarity between the biosignal measured from the user and biosignals of other users.

12. The method of claim 10, wherein whether the condition of the first user indicates infectiousness is determined based on the location information, the biosignal, and environment information of an area corresponding to the location information.

13. The method of claim 12, wherein the environment information comprises at least one of a temperature of the area, a humidity of the area, or a type of a facility located in the area.

14. The method of claim 10, wherein the feedback information comprises an infection expected area in which a spread of an infection is estimated based on movement paths of the users having a condition indicating infection.

15. The method of claim 10, further comprising:
receiving a request to provide the biosignal from the analyzing server in response to a determination that the user visited a target area during a target period.

16. The method of claim 10, wherein users having a condition indicating infection are determined by comparing schedule information of the users to schedule information of a super spreader.

17. The method of claim 10, wherein the feedback information comprises at least one of information on a possibility of infection by a disease, a recommendation to avoid an outdoor activity, or a recommendation associated with an outpatient service.

18. The method of claim 10, wherein the biosignal comprises at least one of temperature information, blood pressure information, heartbeat information, or perspiration information.

19. The method of claim 10, further comprising:
outputting a message of inquiry as to whether the biosignal is provided to the analyzing server in response to the biosignal being different from a reference pattern,
wherein the transmitting comprises transmitting the location information and the biosignal to the analyzing server based on a user input in response to the message.

20. A terminal, comprising:
a sensor integrated in the terminal and configured to measure a biosignal from a first user; and
a communicator integrated in the terminal and configured to transmit the biosignal and simultaneous corresponding location information of the terminal to an analyzing server, and receive feedback information on infectiousness of a condition of the first user from the analyzing server in response to a determination that the condition of the user indicates infectiousness based on the biosignal, wherein:

singular signals are extracted, by the analyzing server, from the biosignals of users of terminals by comparing the biosignals to one or more reference patterns, the one or more reference patterns detected during a health condition of the users being relatively normal;

the infectiousness of the condition of the first user among the users is determined, by the analyzing server, by analyzing a similarity among the singular signals and a similarity among areas corresponding to the corresponding location information;

the first user is classified as a suspected group, by the analyzing server, in response to the determining that the condition of the first user indicates infectiousness, wherein the suspected group comprises users suspected of having a disease condition;

a biosignal of a second user is received, by the analyzing server, the second user being from a definite diagnosis group having a confirmed disease condition;

the users in the suspected group are changed, by the analyzing server, to the definite diagnosis group, based on a comparison of a pattern of a biosignal of the first user and a pattern of the biosignal of the second user.

* * * * *